(12) United States Patent
Hwang et al.

(10) Patent No.: US 6,838,553 B1
(45) Date of Patent: Jan. 4, 2005

(54) PEPTIDE REPEAT IMMUNOGENS

(75) Inventors: Jaulang Hwang, Taipei (TW); Chia-Tse Hsu, Tainan (TW); Chun-Jen Ting, Hsinchu (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/412,558

(22) Filed: Oct. 5, 1999

(51) Int. Cl.⁷ .......................... C07H 21/04; C07H 21/02
(52) U.S. Cl. .................... 536/23.4; 536/23.1; 536/23.7; 536/23.51
(58) Field of Search ............................... 536/23.4, 23.1, 536/23.51, 23.7; 435/69.7, 69.4, 69.3, 69.1; 424/184.1, 192.1; 530/825, 350, 300

(56) References Cited

U.S. PATENT DOCUMENTS

| | | | |
|---|---|---|---|
| 4,892,827 A | * 1/1990 | Pastan et al. ................ | 435/193 |
| 5,648,245 A | 7/1997 | Fire et al. ................... | 435/91.1 |
| 5,668,255 A | 9/1997 | Murphy ....................... | 530/350 |
| 5,830,713 A | 11/1998 | Ferrari et al. ............... | 435/91.1 |
| 6,048,527 A | * 4/2000 | Granoff et al. ........... | 424/150.1 |
| 6,140,066 A | * 10/2000 | Lorberboum-Galski et al. . | 435/7.23 |
| 6,287,568 B1 | * 9/2001 | Wang et al. ............ | 424/197.11 |
| 6,387,684 B1 | * 5/2002 | Hwang et al. ............... | 435/233 |
| 2003/0219459 A1 | * 11/2003 | Bachmann et al. ....... | 424/199.1 |

FOREIGN PATENT DOCUMENTS

| | | | |
|---|---|---|---|
| EP | 0 406 029 A1 | * | 2/1991 |
| WO | WO 91/02799 | * | 3/1991 |
| WO | WO 93/18150 | * | 9/1993 |
| WO | WO 96/24675 | * | 8/1996 |
| WO | WO 97/15325 | * | 5/1997 |

OTHER PUBLICATIONS

Lukac et al. Infect. Immun. 56: 3095–3098, 1988.*
Meloen et al. Vaccine 12: 741–746, 1994.*
Chen et al. Appl. Microbiol. Biotechnol. 52: 524–533, Oct. 1999.*
McGuinnes et al. Mo. Microbiol. 7: 505–514, 1993.*
Gray et al. PNAS 81: 2645–2649, 1984.*

Allured, Viloya S. et al. "Structure of exotoxin A of *Pseudomonas aeruginosa* at 3.0–Ångstrom resolution," Proc. Natl. Acad. Sci. USA, vol. 83, pp. 1320–1324, Mar. 1986.

Chow, Judy T. et al., "Identification of the Carboxyl–terminal Amino Acids Important for the ADP–Ribosylation Activity of Pseudomonas exotoxin A," The Journal of Biological Chemistry, vol. 264, pp. 18818–18823, 1989.

Hwang, Jaulang, et al., "Functional Domains of Pseudomonas Exotoxin Identified by Deletion Analysis of the Gene Expressed in *E. coli*," Cell, vol. 48, pp. 129–136, Jan. 16, 1987.

Hwang, Jaulang et al., "Structure and Function Relationship of Pseudomonas Exotoxin A," The Journal of Biological Chemistry, vol. 264, No. 4, pp. 2379–2384, 1989.

Krambovitis, Elias et al., "Preparation of MUC–1 Oligomers Using an Improved Convergent Solid–phase Peptide Synthesis," The Journal of Biological Chemistry, vol. 273, No. 18, pp. 10874–10879, 1998.

Novella, Isabel S. et al., "Use of substituted and tandemrepeated peptides to probe the relevance of the highly conserved RGD tripeptide in the immune response . . . ," FEBS 12978, vol. 330, No. 3, pp. 253–259, 1993.

White, Michael J. et al., "Concatemer Chain Reaction: A Taq DNA Polymerase–Mediated Mechanism for Generating Long Tandemly Repetitive DNA Sequences," Analytical Biochemistry, vol. 199, pp. 184–190, 1991.

* cited by examiner

*Primary Examiner*—S. Devi
(74) *Attorney, Agent, or Firm*—Fish & Richardson P.C.

(57) ABSTRACT

The invention relates to a polypeptide including (1) a receptor binding domain of a *Pseudomonas* exotoxin A, and (2) at least two copies of a peptide sequence.

4 Claims, 3 Drawing Sheets

Figure 2:
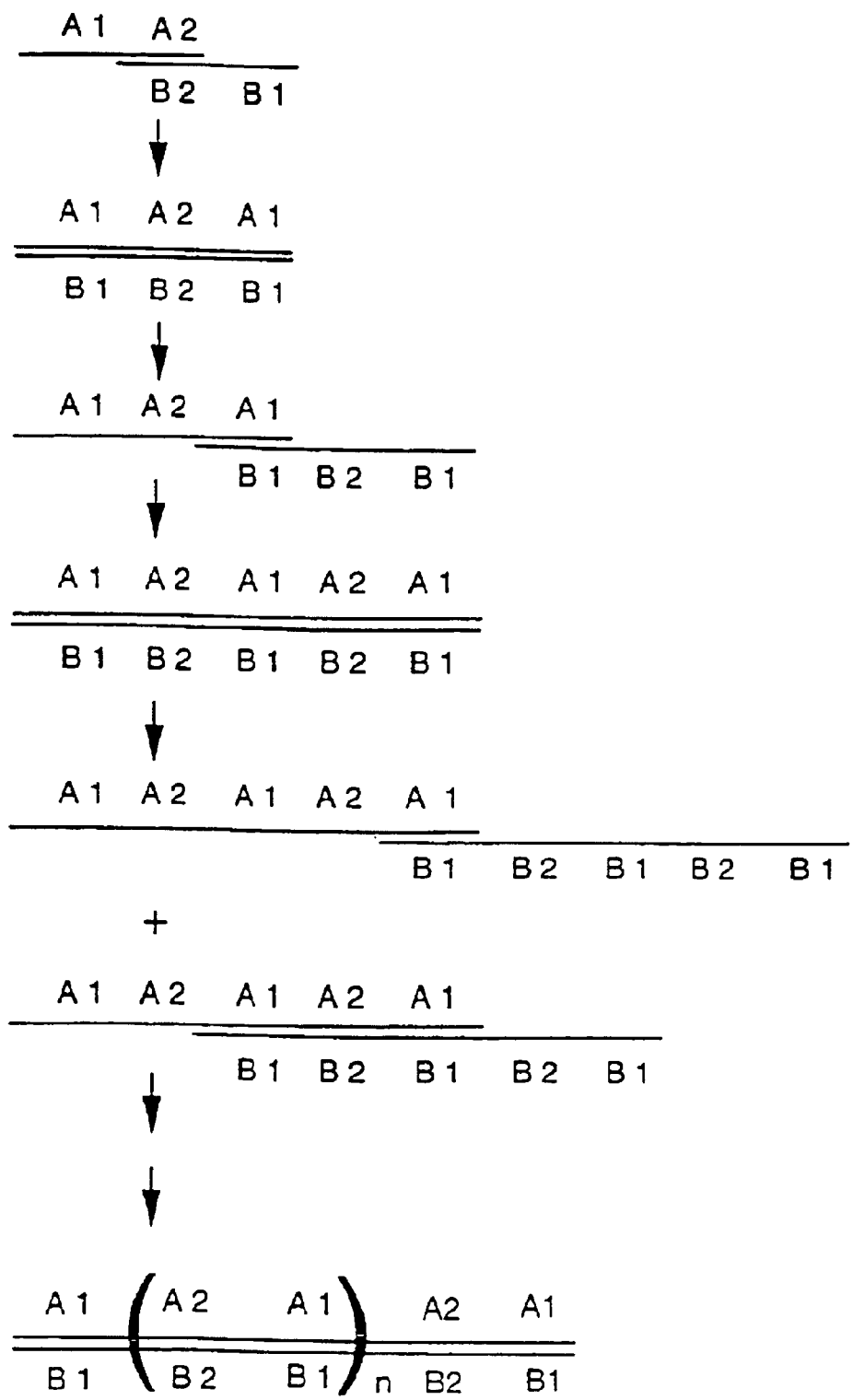

GnRH
Peptide sequence      E   H   W   S   Y   G   L   R   P   G

DNA sequence
```
              A1                      A2
     GAACATTGGTCATAT GGACTACGGGCCGGGA
     CTTGTAACCAGTATA CCTGATGCCGGCCCT
              B1                      B2
```

Primer
```
              A1                      A2
Oligo A  GAACATTGGTCATAT GGACTACGGGCCGGGA
Oligo B                  CCTGATGCCGGCCCT CTTGTAACCAGTATA
                              B2              B1
```

FIG. 1

PEPTIDE REPEAT IMMUNOGENS

BACKGROUND OF THE INVENTION

The successful development of a protein-based vaccine often requires a delicate balance between enhancing immunogenicity of a particular antigen and the potential toxicity elicited by such enhancing. For example, an effective adjuvant used in animal studies (e.g., complete Freund's) may be too toxic to be used in vaccines prepared for humans.

SUMMARY OF THE INVENTION

The invention is based on the discovery of a new means of generating an immune response to a peptide antigen by concatemerizing the peptide and fusing the concatemer to a receptor binding domain of a *Pseudomonas* exotoxin. Such a fusion protein elicits antigen-specific antibodies in a variety of mammals, with little or no toxicity observed.

Accordingly, the invention features a polypeptide including (1) at least two copies (e.g., at least 12 or 16 copies) of a peptide sequence, and (2) a receptor binding domain of a *Pseudomonas* exotoxin A.

The peptide sequence must be at least two amino acids in length (e.g., at least 3, 5, 7, 9, or 10 amino acids in length). In a preferred embodiment, the peptide sequence can be less than 1000 amino acids in length (e.g., less than 500, 100, 50, or 20 amino acids in length). The peptide sequence can include any antigen in which an immune response against it is beneficial, such as gonadotropin releasing hormone or GnRH (e.g., EHWSYGLRPG [SEQ ID NO:1]) or a fragment of a vaccinia virus coat protein (e.g., LIGICVAVTVAI [SEQ ID NO:2]).

A receptor binding domain is an amino acid sequence within a polypeptide which specifically binds to a LDL/alpha$_2$-microglobulin cell receptor. An example of a receptor binding domain is amino acids 1–252 (domain Ia) of the *P. aeruginosa* exotoxin A (PE):

mhliphwiplvaslgllaggssasaaeeafdlwnecakacvldlk dgvrssrmsvdpaiadtngqgvlhysmvleggndalklaidnals itsdgltirleggvepnkpvrysytrqargswslnwlvpighekp snikvfihelnagnqlshmspiytiemgdellaklardatffvra hesnemqptlaishagvsvvmaqtqprrekrwsewasgkylclld pldgvynylaqqrcnlddtwegkiyrv (SEQ ID NO:3).

Variants of the sequence immediately above, including substitutions, deletions, or additions are permissible, provided that the receptor binding domain specifically binds to a LDL/alpha$_2$-microglobulin cell receptor.

The position of the various elements within the polypeptide can be varied, as long the polypeptide is still able to elicit an immune response in a mammal. For example, all copies of the peptide sequence can be in a consecutive series, meaning that all copies occur as a single block of peptide repeats without intervening amino acids in between any two copies. In addition, the receptor binding domain can occur anywhere in the polypeptide (e.g., at the N-terminus, at the C-terminus, internal, or between two copies of the peptide sequence), as long as the intended function of the polypeptide as an antigen is not disrupted.

The invention also includes nucleic acids (e.g., expression vectors, including viral vectors) that encode a polypeptide of the invention. Such nucleic acids can be used in a naked DNA-based vaccines or to produce the polypeptides of the invention in large quantities.

In addition, the invention features a method of producing a polypeptide by (1) providing a nucleic acid of the invention, (2) introducing the nucleic acid into a cell (e.g., a bacteria or eukaryotic cell, including cell lines and primary cells), and (3) expressing the polypeptide in the cell.

The polypeptides and nucleic acids of the invention can be used to provide new antigens and vaccines for eliciting an immune response against specific peptide sequences. These antigens can be formulated as safe and effective vaccines in mammals and humans, or at the very least, tested for efficacy in human and/or animal models, including primate animal models.

Other features or advantages of the present invention will be apparent from the following drawings and detailed description, and also from the claims.

BRIEF DESCRIPTION OF THE DRAWING

FIG. 1 is a representation of a GnRH peptide sequence (SEQ ID NO:1) useful in the polypeptides of the invention and primer sequences (SEQ ID NO:4 for Oligo A; SEQ ID NO:5 for Oligo B) which encode it or portions thereof (DNA sequence A1 and A2 is designated SEQ ID NO:4; DNA sequence B1 and B2 is designated SEQ ID NO:12).

FIG. 2 is a representation of how successive extension, denaturation, and annealing (i.e., PCR) of the primers in FIG. 1 produce a nucleic acid encoding concatamers of the peptide sequence.

FIG. 3 is a representation of a final PCR amplification of the concatemeric nucleic acid shown in FIG. 2 to introduce at the ends of the concatemer a stop codon and suitable restriction sites for cloning. Adaptor primer A is designated SEQ ID NO:6. Adaptor primer B is designated SEQ ID NO:7. The 5' overhang sequence containing the EcORI site is designated SEQ ID NO:8 (complimentary strand is designated SEQ ID NO:11). The 5' overhang sequence containing the SacII site is designated SEQ ID NO:9 (complimentary strand is designated SEQ ID NO:10).

DETAILED DESCRIPTION

The invention relates to new polypeptides having multiple copies of a peptide antigen fused to the receptor binding domain of a *Pseudomonas* exotoxin. Multiple copies of a peptide antigen is believed to increase immunologic presentation of epitopes present in each monomeric peptide sequence, though the mechanism is unclear. In addition, the exotoxin fragment is believed to increase binding between the polypeptide and antigen presenting cells, thereby facilitating uptake and presentation of peptide sequences.

I. Generation of Antibodies

The polypeptides of the invention can be used to generate antibodies that specifically bind a monomeric peptide sequence. Such antibodies can be used in diagnostic and/or therapeutic procedures that require the enhancement, inhibition, or detection of any molecule which contains the epitope presented by the peptide sequence.

In particular, various host animals can be immunized by injection of a composition containing a polypeptide of the invention. Host animals can include rabbits, mice, guinea pigs, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Coxynebacterium parvum*.

Antibodies include polyclonal antibodies, monoclonal antibodies, humanized or chimeric antibodies, single chain antibodies, Fab fragments, F(ab'), fragments, and molecules produced using a Fab expression library.

Monoclonal antibodies, which are homogeneous populations of antibodies to a particular antigen, can be prepared using the polypeptides described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In: Monoclonal Antibodies and T Cell Hybridomas, Elsevier, N.Y., 1981; U.S. Pat. No. 4,376,110; Kosbor et al., Immunology Today 4:72, 1983; Cole et al., Proc. Natl. Acad. Sci. USA 80:2026, 1983; and Cole et al., Monoclonal Antibodies and Cancer Therapy, Alan R. Liss, Inc., pp. 77–96, 1983). Such antibodies can be of any immunoglobulin class including IgG, IgM, IgE, IgA, IgD and any subclass thereof. The hybridoma producing the Mab of this invention may be cultivated in vitro or in vivo. The ability to produce high titers of mAbs in vivo makes this an excellent method of production.

The antibodies can be used, for example, to detect the presence of an antigen in a biological sample as part of a diagnostic assay, and also to evaluate the effectiveness of medical treatments by other therapeutic approaches.

In addition, techniques developed for the production of "chimeric antibodies" (Morrison et al., Proc. Natl. Acad. Sci. USA 81:6851, 1984; Neuberger et al., Nature 312:604, 1984; Takeda et al., Nature 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine Mab and a human immunoglobulin constant region.

Alternatively, techniques described for the production of single chain antibodies (U.S. Pat. Nos. 4,946,778, 4,946,778, and 4,704,692) can be adapted to produce single chain antibodies against a particular peptide antigen. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include, but are not limited to, $F(ab')_2$ fragments that can be produced by pepsin digestion of the antibody molecule, and Fab fragments that can be generated by reducing the disulfide bridges of $F(ab')_2$ fragments.

II. Production and Use of Vaccine Compositions

The invention includes vaccine compositions (e.g., parenteral injectable vaccines) containing at least one polypeptide of the invention and, optionally, a pharmaceutically acceptable carrier, such as the diluents phosphate buffered saline or a bicarbonate solution (e.g., 0.24 M $NaHCO_3$). The carriers used in the composition are selected on the basis of the mode and route of administration, and standard pharmaceutical practice. Suitable pharmaceutical carriers and diluents, as well as pharmaceutical necessities for their use, are described in Remington's Pharmaceutical Sciences. An adjuvant, e.g., a cholera toxin, *Escherichia coli* heat-labile enterotoxin (LT), liposome, or immune-stimulating complex (ISCOM), can also be included in the new vaccine composition, if necessary.

The amount of vaccine administered will depend, for example, on the particular peptide antigen in the polypeptide, whether an adjuvant is co-administered with the antigen, the type of adjuvant co-administered, the mode and frequency of administration, and the desired effect (e.g., protection or treatment), as can be determined by one skilled in the art. In general, the new vaccine antigens are administered in amounts ranging between 1 μg and 100 mg polypeptide per adult human dose. If adjuvants are administered with the vaccines, amounts ranging between 1 ng and 1 mg per adult human dose can generally be used. Administration is repeated as necessary, as can be determined by one skilled in the art. For example, a priming dose can be followed by three booster doses at weekly intervals. A booster shot can be given at 8 to 12 weeks after the first immunization, and a second booster can be given at 16 to 20 weeks, using the same formulation. Sera or T-cells can be taken from the individual for testing the immune response elicited by the vaccine against the neurotoxin. Methods of assaying antibodies or cytotoxic T cells against a specific antigen are well known in the art. Additional boosters can be given as needed. By varying the amount of polypeptide, the copy number of peptide antigen in the polypeptide, and frequency of administration, the immunization protocol can be optimized for eliciting a maximal immune response.

Before administering the above compositions in humans, toxicity and efficacy testing in animals are desirable. In an example of efficacy testing, mice (e.g., Swiss-Webster mice) can be vaccinated via an oral or parenteral route with a composition containing a polypeptide of the invention. For vaccines against an infectious agent, after the initial vaccination or after optional booster vaccinations, the mice (and corresponding control mice receiving mock vaccinations) are challenged with a $LD_{95}$ dose of the infectious agent. End points other than lethality can also be used. Efficacy is determined if mice receiving the vaccine die at a rate lower than the mock-vaccinated mice. Preferably, the difference in death rates should be statistically significant. Rabbits can be used in the above testing procedure instead of mice.

Alternatively, the new vaccine compositions can be administered as ISCOMs. Protective immunity has been generated in a variety of experimental models of infection, including *toxoplasmosis* and Epstein-Barr virus-induced tumors, using ISCOMS as the delivery vehicle for antigens (Mowat et al., Immunology Today 12:383–385, 1991). Doses of antigen as low as 1 μg encapsulated in ISCOMs have been found to produce class I mediated cytotoxic T cell responses (Takahashi et al., Nature 344:873–875, 1990).

Without further elaboration, it is believed that one skilled in the art can, based on the above disclosure and the description below, utilize the present invention to its fullest extent. The following examples are to be construed as merely illustrative of how one skilled in the art can practice the invention and are not limitative of the remainder of the disclosure in any way. Any publications cited in this disclosure are hereby incorporated by reference.

EXAMPLE 1

A Multimeric Vaccine Against Gonadotropin Releasing Hormone

Gonadotropin releasing hormone (GnRH) is a decapeptide produced by the arcuate nuclei of the hypothalamus and regulates expression of luteinizing hormone and follicle-stimulating hormone, which in turn regulates gonad development in humans. In addition, increased expression of GnRH and its receptor has been correlated with a variety of tumors, including cancer of the breast, ovary, endometrium, and prostate. See, e.g., Imai et al., Cancer 74:2555–2561, 1994; Eidne et al., J. Clin. Endocrinol. Metab. 64:425–432, 1987; and Irmer et al., Cancer Res. 55:817–822, 1995.

Therefore, antibodies against GnRH may provide a means to modulate reproductive hormone activity and/or cancer development and progression.

Figure 3:
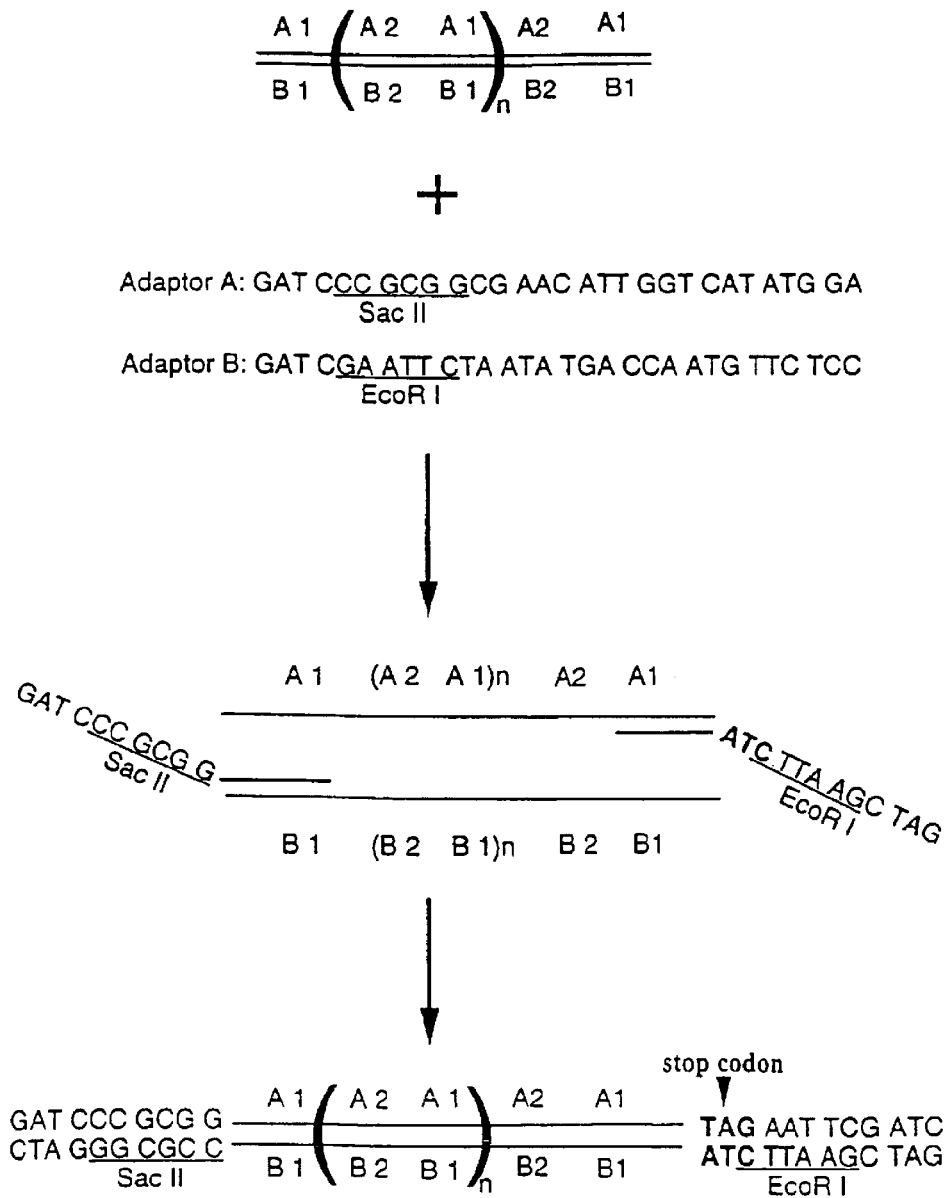

To produce an antigen containing concatamers of GnRH fused to a receptor binding domain, the following approach, as outlined in FIGS. 1–3, was used. This procedure was designated template repeat PCR (TRPCR).

Two oligonucleotides were designed for TRPCR (FIG. 1). Oligo A encoded target antigen GnRH. Oligo B was complementary to oligo A. Oligo A is dissected into 5' half A1 and 3' half A2, both halves being of equal lengths. Oligo B is dissected into 5' half B1 and 3' half B2, again both halves being of equal lengths. A1 was complementary to B1, while A2 was complementary to B2.

The thermal cycler was programmed for denaturation at 94° C. for 30 seconds, annealing at 37° C. for 30 seconds, and extension at 72° C. for 30 seconds. Using oligos A and B, PCR was performed for 30 cycles, followed by a final extension at 72° C. for 10 minutes. This PCR should produced DNA species containing repeated sequences encoding GnRH, as illustrated in FIG. 2.

Two adapter primers (Adaptor A and Adaptor B) were designed to add an appropriate stop codon at the end of the repeated open reading frame (ORF) and two suitable restriction sites flanking the ORF (FIG. 3). For this step (which was designated adaptor PCR), the template for the PCR was a 100-fold dilution of the TRPCR product produced as described above. The thermal cycler was programmed as described above, except that the denaturation was set for 1 minute instead of 30 seconds. The resulting PCR product contained a SacII site at the 5' end, an EcORI site at the 3' end, and a stop codon at the end of the ORF.

The products of TRPCR and adaptor-PCR were then examined on a polyacrylamide gel. The majority of the TRPCR products were 500 bp to 700 bp in length. After adaptor PCR, products were distributed in a ladder, the lowest band containing the dimer of the GnRH DNA repeat and the slower migrating bands containing higher order multimers. The number of repeats present ranged from 3 to at least 12. One clone containing 12 repeats of GnRH coding sequence was chosen for further study.

The DNA fragment encoding 12 repeats of GnRH was subcloned into plasmid PPEDI, which was produced by subcloning the sequence encoding domain Ia of PE in pJH14 (Hwang et al., J. Biol. Chem. 264:2379–2384, 1989) into pET (Novagen). This plasmid expresses a polypeptide containing domain Ia of PE, which includes the toxin receptor binding domain of the toxin, and contains a $His_6$ tag at its N-terminus. The GnRH repeats were inserted at the 3' end of PE structure gene to produce pPEDIG12. The protein produced by this expression plasmid was designated PEIa-GnRH12.

pPEDIG12 was transformed into BL21(DE3)lysS. The transformants were cultured at 37° C. in LB medium containing ampicillin (50 $\mu$g/ml), chloramphenicol (25 $\mu$g/ml) and tetracycline (10 $\mu$g/ml). When the $A_{600}$ of the culture reached 0.2, IPTG was added to the culture to medium to achieve a final concentration of 0.1 mM. Cells were cultured for another 90 minutes and then harvested. Since PEIa-GnRH12 is overexpressed in the form of inclusion bodies, the cells were extracted with 6 M urea.

The extracts were then purified using the Novagen pET His-Tag System. The fractions containing PEIa-GnRH12 were collected and dialysed against 50 mM ammonium acetate (pH 4.0). PEIa-GnRH12 was stable for at least 6 months when stored at 4° C. After nickel-agarose affinity column chromatography, PEIa-GnRH12 was isolated to about 95% purity, as determined by SDS-PAGE.

To test this new immunogen, six week old New Zealand female rabbits were immunized with PEIa-GnRH12. A 0.5 ml bolus containing 100 $\mu$g of PEIa-GnRH12 and 125 $\mu$g aluminum phosphate (pH 7.0) was injected into the rabbit at the first time point (six weeks after birth). One week after the first immunization, an identical 0.5 ml bolus was injected into the rabbits for a second immunization, followed by an identical injection two weeks after the first immunization. After the three immunizations, sera were collected for ELISA and immunoblotting analysis. To test whether antibodies against the multimeric antigen was directed to monomeric epitopes or to epitopes spanning the junction between monomers, several GST fusion proteins containing various multimers of GnRH were produced as targets for ELISA.

The antibodies produced in the immunized rabbits failed to recognize with GST alone, while the sera at 5,000-fold dilution recognized all GST-GnRH fusion proteins to the same extent, irrespectively of how many GnRH repeats the GST fusion proteins contained. These results suggested that most of the antibodies produced in response to the immunogen recognized monomeric GnRH epitopes rather than any hybrid epitopes created by concatemerization.

GST-GnRH1 and GST-GnRH5 were specifically used as ELISA targets. Sera from thrice immunized rabbits, diluted 10,000-fold, recognized GST-GnRH1 and GST-GnRH5 to the same extent, thereby confirming that the immune response against the immunogen was directed to GnRH monomer-specific epitopes.

To confirm that the antibodies elicited by the new immunogen was physiologically active, immunized rabbits were monitored for ovary development. As a control, rabbits were also immunized with PEIa-TopN8, a polypeptide containing domain Ia of PE fused to 8 repeats of a 10-amino acid topoisomerase N-terminal peptide. The PEIa-TopN8-immunized rabbits showed normal ovary development, while the ovaries of PEIa-GnRH12-immunized rabbits were significantly decreased in size. Thus, the GnRH immunogen produced can be used as an immunogen to induce autoantibodies useful for treating GnRH-associated diseases.

To further confirm the utility of the new GnRH immunogen, mice and a pig were also immunized with PEIa-GnRH12. The mice immunization regimen was identical to the rabbit immunization described above, except that each mouse received a 100 $\mu$l bolus containing 10 $\mu$g PEIa-GnRH12 and 25 $\mu$g aluminum phosphate (pH 7.0) for each injection. In addition, a 24 day-old pig was injection once with a 1 ml bolus containing 10 mg PEIa-GnRH12 and 250 $\mu$g aluminum phosphate (pH 7.0). GnRH-specific antibodies were readily elicited in the mice and pig, as well as in rabbits, indicating that the antigens can elicit an immune response in a variety of animals. Further, a single immunization was sufficient to elicit an immune response.

EXAMPLE 2

A Multimeric Vaccine Against Vaccinia Virus

Instead of a GnRH peptide sequence, a DNA sequence containing a repeat of the vaccinia virus coat protein peptide LIGICVAVTVAI (SEQ ID NO:2) was constructed using PCR as described in Example 1 above. A PE fusion protein containing 16 repeats of the virus coat protein peptide was produced and purified according to the procedures in Example 1.

Six-week old rabbits were injected with a 1 ml bolus containing 100 $\mu$g viral peptide repeat antigen and 100 $\mu$g complete Freund's adjuvant. Four weeks later, the rabbits received a second 1 ml injection containing 100 μg antigen and 100 μg incomplete Freund's adjuvant. At 8 weeks after the first immunization, the rabbits were injected with a 1 ml bolus containing 100 μg antigen (no adjuvant). Rabbits thrice immunized with the virus coat protein immunogen produced vaccinia virus-specific antibodies.

Thus, the general procedure of linking a peptide repeat to a PE receptor binding domain was shown to be successful for a second peptide.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. An isolated nucleic acid encoding a polypeptide, wherein the polypeptide comprises (1) a *Pseudomonas* exotoxin A fragment consisting of the receptor binding domain of the *Pseudomonas* exotoxin A and (2) at least two copies of an antigenic peptide sequence wherein said copies occur as a single block of peptide repeats without intervening amino acids in between any two copies.

2. An isolated nucleic acid encoding a polypeptide, wherein the polypeptide comprises (1) a *Pseudomonas* exotoxin A fragment consisting of the receptor binding domain of a *Pseudomonas* exotoxin A and (2) at least two copies of an antigenic peptide sequence comprising SEQ ID NO:1, and has no toxicity.

3. An isolated nucleic acid encoding a polypeptide, wherein the polypeptide comprises (1) a *Pseudomonas* exotoxin A fragment consisting of the receptor binding domain of a *Pseudomonas* exotoxin A and (2) 10 to 20 copies of an antigenic peptide sequence, and has no toxicity.

4. An isolated nucleic acid encoding a polypeptide, wherein the polypeptide comprises (1) a *Pseudomonas* exotoxin A fragment consisting of the receptor binding domain of a *Pseudomonas* exotoxin A and (2) at least two copies of an antigenic peptide sequence in a consecutive series, and has no toxicity.

* * * * *

SEQUENCE LISTING

```
<160> NUMBER OF SEQ ID NOS: 12

<210> SEQ ID NO 1
<211> LENGTH: 10
<212> TYPE: PRT
<213> ORGANISM: Homo sapiens

<400> SEQUENCE: 1

Glu His Trp Ser Tyr Gly Leu Arg Pro Gly
1               5                   10

<210> SEQ ID NO 2
<211> LENGTH: 12
<212> TYPE: PRT
<213> ORGANISM: Vaccinia virus

<400> SEQUENCE: 2

Leu Ile Gly Ile Cys Val Ala Val Thr Val Ala Ile
1               5                   10

<210> SEQ ID NO 3
<211> LENGTH: 252
<212> TYPE: PRT
<213> ORGANISM: Pseudomonas aeruginosa

<400> SEQUENCE: 3

Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
                20                  25                  30

Trp Asn Glu Cys Ala Lys Ala Cys Val Leu Asp Leu Lys Asp Gly Val
            35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
            115                 120                 125

Pro Ile Gly His Glu Lys Pro Ser Asn Ile Lys Val Phe Ile His Glu
        130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
```

```
                  165                 170                 175
    Phe Val Arg Ala His Glu Ser Asn Glu Met Gln Pro Thr Leu Ala Ile
                180                 185                 190

Ser His Ala Gly Val Ser Val Val Met Ala Gln Thr Gln Pro Arg Arg
            195                 200                 205

Glu Lys Arg Trp Ser Glu Trp Ala Ser Gly Lys Val Leu Cys Leu Leu
        210                 215                 220

Asp Pro Leu Asp Gly Val Tyr Asn Tyr Leu Ala Gln Gln Arg Cys Asn
    225                 230                 235                 240

Leu Asp Asp Thr Trp Glu Gly Lys Ile Tyr Arg Val
                    245                 250

<210> SEQ ID NO 4
<211> LENGTH: 30
<212> TYPE: DNA
<213> ORGANISM: Artificial Sequence
<220> FEATURE:
<223> OTHER INFORMATION: Synthetically generated primer

<400> SEQUENCE: 4
gaacattggt catatggact acggccggga                                          30

<210> SEQ ID NO 5
<211> LENGTH: 30
<212> TYPE: DNA
<213> ORGANISM: Artificial Sequence
<220> FEATURE:
<223> OTHER INFORMATION: Synthetically generated primer

<400> SEQUENCE: 5
cctgatgccg gccctcttgt aaccagtata                                          30

<210> SEQ ID NO 6
<211> LENGTH: 29
<212> TYPE: DNA
<213> ORGANISM: Artificial Sequence
<220> FEATURE:
<223> OTHER INFORMATION: Synthetically generated primer

<400> SEQUENCE: 6
gatcccgcgg cgaacattgg tcatatgga                                           29

<210> SEQ ID NO 7
<211> LENGTH: 30
<212> TYPE: DNA
<213> ORGANISM: Artificial Sequence
<220> FEATURE:
<223> OTHER INFORMATION: Synthetically generated primer

<400> SEQUENCE: 7
gatcgaattc taatatgacc aatgttctcc                                          30

<210> SEQ ID NO 8
<211> LENGTH: 12
<212> TYPE: DNA
<213> ORGANISM: Artificial Sequence
<220> FEATURE:
<223> OTHER INFORMATION: Synthetically generated primer

<400> SEQUENCE: 8
gatcgaattc ta                                                             12

<210> SEQ ID NO 9
```

```
<211> LENGTH: 10
<212> TYPE: DNA
<213> ORGANISM: Artificial Sequence
<220> FEATURE:
<223> OTHER INFORMATION: Synthetically generated primer

<400> SEQUENCE: 9
gatcccgcgg                                                          10

<210> SEQ ID NO 10
<211> LENGTH: 10
<212> TYPE: DNA
<213> ORGANISM: Artificial Sequence
<220> FEATURE:
<223> OTHER INFORMATION: Synthetically generated primer

<400> SEQUENCE: 10
ccgcgggatc                                                          10

<210> SEQ ID NO 11
<211> LENGTH: 12
<212> TYPE: DNA
<213> ORGANISM: Artificial Sequence
<220> FEATURE:
<223> OTHER INFORMATION: Synthetically generated primer

<400> SEQUENCE: 11
tagaattcga tc                                                       12

<210> SEQ ID NO 12
<211> LENGTH: 30
<212> TYPE: DNA
<213> ORGANISM: Artificial Sequence
<220> FEATURE:
<223> OTHER INFORMATION: Synthetically generated primer

<400> SEQUENCE: 12
cttgtaacca gtatacctga tgccggccct                                    30
```